(12) United States Patent
Salva Calcagno

(10) Patent No.: US 6,659,038 B2
(45) Date of Patent: Dec. 9, 2003

(54) SAFETY IDENTIFICATION DEVICE

(75) Inventor: Eduardo Luis Salva Calcagno, Buenos Aires (AR)

(73) Assignee: Duwimax International S.A., Montevideo (UY)

( * ) Notice: Subject to any disclaimer, the term of this patent is extended or adjusted under 35 U.S.C. 154(b) by 0 days.

(21) Appl. No.: 09/961,261

(22) Filed: Sep. 25, 2001

(65) Prior Publication Data

US 2002/0037094 A1 Mar. 28, 2002

(30) Foreign Application Priority Data

Sep. 26, 2000 (AR) .................................. P 00 01 05051

(51) Int. Cl.[7] ................................................ B41K 1/00
(52) U.S. Cl. ......................................... 118/31.5; 427/1
(58) Field of Search ............................ 118/31.5; 427/1; 382/124, 129

(56) References Cited

U.S. PATENT DOCUMENTS

| | | | | | |
|---|---|---|---|---|---|
| 1,833,287 A | * | 11/1931 | Hadley | ......................... | 524/77 |
| 3,089,459 A | * | 5/1963 | Picard | ......................... | 118/31.5 |
| 3,664,910 A | * | 5/1972 | Hollie | ......................... | 428/41.7 |
| 4,202,120 A | * | 5/1980 | Engel | ......................... | 283/99 |
| 4,706,600 A | * | 11/1987 | Mason et al. | ............... | 118/31.5 |
| 5,143,551 A | * | 9/1992 | Mason et al. | ............... | 118/31.5 |

* cited by examiner

*Primary Examiner*—Laura Edwards
(74) *Attorney, Agent, or Firm*—Jacobson Holman PLLC

(57) ABSTRACT

Safety identification device for collecting fingerprints and DNA related material from an individual, for use in verifying the identity of an individual, such as in documents and forms. The device includes at least one layer for collecting and retaining the fingerprint and the material from the individual, and at least another layer attached to the at least one layer for protecting and preserving the material for determining the DNA of the individual.

16 Claims, 3 Drawing Sheets

SAFETY IDENTIFICATION DEVICE

BACKGROUND OF THE INVENTION

1. Field of the Invention

The present invention relates to the field of identification of individuals and, more particularly refers to a new device for assisting in the identification of an individual by collecting and safely maintaining a biometric characteristic of the individual. Even more particularly, the invention involves a device for recording a fingerprint by placing a fingertip under pressure onto the device and obtaining a print of the grooves pattern in the finger pulp, and keeping the fingerprint inalterable, under protection and shelter, for identification purposes. The inventive devive provides an adhesive surface to place the finger tip in order to retain a stamp of the fingerprint as well as particular, minute material, such as dead epithelial cells, fat, sweat, and debris adhered to the finger tip, for use in methods and procedures of certifying identification of individuals in documents, forms, data bases, based not only in the identification of the fingerprint pattern but also of the individual's DNA, thus providing a double safety means for preventing falsification of personal and public documents. This is useful in legitimating property documents, identities, signatures and licenses, such as ID cards, driver license, passports, etc.

2. Description of the Prior Art

It is well known to provide a plurality of means and procedures for identifying individuals and for controlling and certifying the authenticity of documents, such as bank forms and applications. Those means and techniques are disclosed in Argentine Publications Nos. 960101195, 960105399, 970101640 and 970101641, and U.S. Pat. Nos. 245,637 and 246,630, however these procedures fail to provide a simple and straightforward means for legitimate forms, documents, licenses, signatures and ID cards, as well as these techniques are expensive and not effective.

In addition to the foregoing, the techniques and methods for stamping and registering fingerprints require of inks, paints, sprays, etc, all resulting in the need of the individual to count on a toilet or a basin for washing the hands, some times, with the assistance of strong detersive components. It is also frequent that, when the finger tip is placed onto the surface of paper for printing the fingerprint the ink is spread excessively over the surface thus providing a print that does not correspond exactly to the groove pattern of the fingertip pulp.

The typical methods for obtaining fingerprints only provides a print of the superficial pattern of the grooves in the finger pulp without providing information about the depth of the grooves and epithelial lines. Since the obtained print is just a plain drawing, several errors are committed when measuring the distances between adjacent lines corresponding to the crests of the epithelial lines.

Argentine Patent No. 960101195 discloses a system for safe authentication and control of banking documents, credit instruments or registered documents, wherein the system comprises a personal document provided with a microprocessor for storing a personal identification code (CIP) of the individual, also providing biometric characteristics of the individual and several means for issuing and validating documents. The system comprises a device for recording a biometric characteristic of the individual on the basis of which a personal identification code is generated as a cryptographic key and said data is associated to a mathematical expression of the data from the fingerprints of at least one finger of the individual under identification, therefore, a means is obtained for comparing the collected information and the information from the mathematical relation. This system uses the fingerprint of the individual to get a CIP with certain components and procedures, however, the system fails to provide effective results and is easily falsifiable by hackers when entered into the web. In addition, the system does not provide the data about the depth of the finger pulp grooves and no information for determining the DNA is obtained.

Argentine Patent No. 960105399 discloses an auto-adhesive tape or label comprising a stationary part and a moving part defining two faces with printed identification indicia, however the components are complex and fails to provide efficiency for the guarantying and certifying of identities.

It would be therefore convenient to have device capable of easily obtaining the print of a finger pulp with all its parameters involved in the print, in addition to matter from the individual under identification with the purpose of determining the DNA of the individual.

3. Summary of the Invention

It is therefore an object of the present invention to provide a safety identification device comprising at least one layer for collecting and retaining a fingerprint and matter of an individual, and at least another layer attached to the at least one layer for protecting and preserving the matter for determining the DNA of the individual.

It is still another object of the present invention to provide a safety identification device for collecting finger prints and DNA-identifiable material from an individual, for use in guarantying and certifying the identification of an individual in documents and forms, the device comprising a base layer, an intermediate layer for collecting and retaining a fingerprint, particles and debris from a finger of an individual, the particles and debris being apt to determine the DNA of the individual, and a cover layer for covering and sheltering the fingerprint, particles and debris retained in the intermediate layer.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
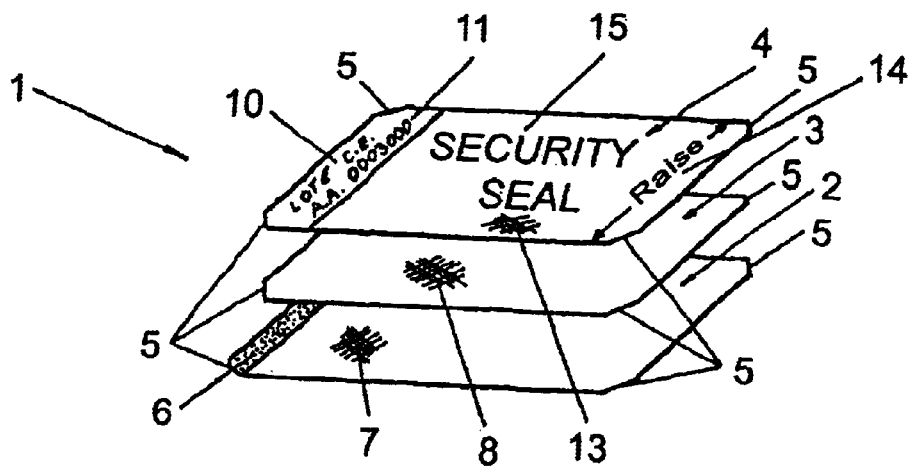
FIG. 1 shows an exploded perspective view of an identification device according to the invention wherein the main three layers of the device may be clearly seen.
Figure 2:
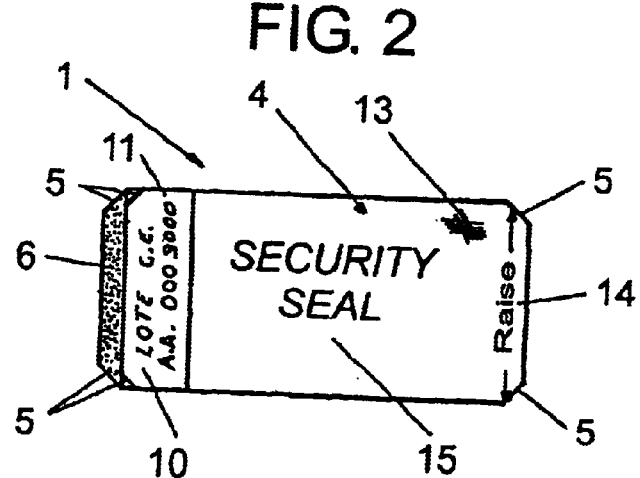
FIG. 2 shows a top plan view of the device of FIG. 1.

Now referring in detail to the drawings it may be seen from FIGS. 1 to 9, a device according to a preferred embodiment of the invention, comprising a safety sticker, also called a stamp or seal, for recording a fingerprint and for being attached to personal, public, commercial, etc. forms, documents, multi-key cards (PIN-OUT), for use in the web and other fields, with the purpose of preventing any deceitful act attempted to be carried out under a fake identity.

The device 1 according to the invention comprises three layers, preferably sheets and/or films, attached one onto the other into a peelable arrangement having a rectangular shape, with long sides having 55–65 mm and short sides having 25–35 mm and with corners 5 being cut or slant at about 135°.

The safety identification device for collecting finger prints and DNA-identifiable material from an individual comprises a base layer 2, an intermediate layer 3, for collecting and retaining a fingerprint, particles and debris from a finger of an individual, the particles and debris being apt to determine the DNA of the individual, and a cover layer 4 for covering and sheltering the fingerprint, particles and debris retained in the intermediate layer.

Base layer 2 is a base sheet made of high resistant high density glassine super-calendered Kraft paper having an inner smooth semi-glossy face 7 including silicone or treated with silicone, the base sheet having an trapezoidal tongue 6 extending from a short side or end of the base sheet and in the same plane of the base sheet for peeling out the base sheet from the peelable arrangement. Tongue 3 extends about 3 mm out or beyond the end of the base layer for permitting an user to take the tongue and pull out the same in order to peel base layer 2 off intermediate layer 3, as shown by the arrow in FIG. 3. The Kraft paper has a weight of 76–85 g/m2, a longitudinal tensile strength of 1.5–20 Kg/inch, and a transverse tensile strength of 7.5–11 Kg/inch.

The second component or layer 3 is located at the center of the arrangement and comprises a double sided A-108 support material comprising a non thermally sealable polypropylene film having a tensile strength of 1400 kg/square inch, a weight of about 11 kg/square meter, a thicknes of about 12.5$\mu$) and crystal color. The film also has two treated faces or sides, namely an upper or top face 8 entering into contact with inner face 9 of layer 4, and a lower or bottom side or face in contact with an inner face 7 of base layer 2.

Figure 7:
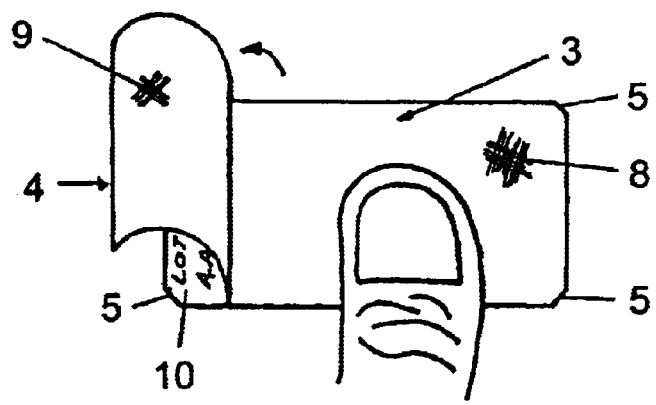
FIG. 7 shows a top perspective view of the device of FIG. 6 with a fingertip placed onto the intermediate layer, according to a preferred use of the invention.

Both faces, upper face 8 and lower face, of the intermediate layer are provided with an adhesive comprising a aqueous dispersed acrylate polymer modified with A-108 synthetic components and having an adhesiveness of 750 g/inch, the adhesive being of the semi-hard-type to hard-type, and having high cohesive properties at 24 h. The adhesive also has a loop tack of 950 g/inch and, in the lower face, is protected by base layer 2. Thus, the lower face of the intermediate layer is capable of being applied onto any surface to be adhered thereto, the adhesive in the upper face permitting to put a finger tip, as shown in FIG. 7, to record a fingerprint 12 with the epithelial lines, retaining a detail of the thickness and depth of said lines as well as retaining epithelial particles and debris, dead cells, finger skin humidity, finger skin fat, all for determining the DNA of an individual finger.

Layer 4 defines the third component or layer and comprises a high strength, high density glassine-type super-calendered Kraft paper having a generally crystalline-white color, with a weight of 62–67 g/square meter, a thickness of 55.8$\mu$ and a break strength of 17 kg/inch. The Kraft paper also has an outer face 13 and an inner face 9, the outer face being transparent and provided or treated with silicone for receiving a printed indicia 14, 15, wherein the indicia may comprise code numbers and personal data for storing in a data base and a computer. Inner face 9 is treated with paraffin to prevent the paper 4 from being adhered to the adhesive-containing upper face 8 of intermediate layer film 3. Indicia may comprise With base layer 2 adhered to the lower face of intermediate layer film 3 and cover layer 4 adhered to the upper face of the intermediate layer film, the upper and lower faces of the intermediate layer remain covered and protected any spoiling environment, and these faces are prevented from being strongly adhered to the layers thus preserving the adhesive properties of the adhesive up to the moment the device is used.

Figure 6:
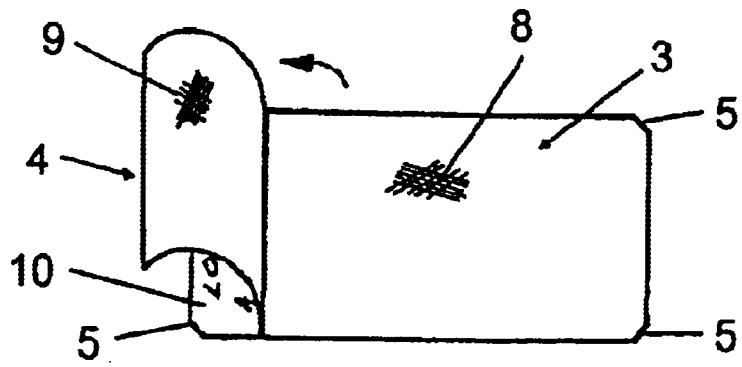
FIG. 6 shows a top perspective view of the device of FIG. 5 with the cover layer being entirely peeled up from the intermediate layer and the device is ready for use.
Figure 8:
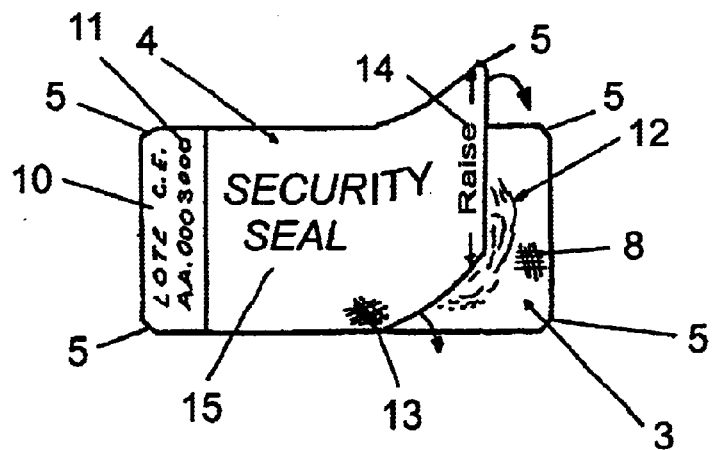
FIG. 8 shows a top perspective view of the device of FIG. 7 with the cover layer being partially peeled from the intermediate layer but moving towards the intermediate layer to adhere the same and cover the fingerprint in the intermediate layer.
Figure 9:
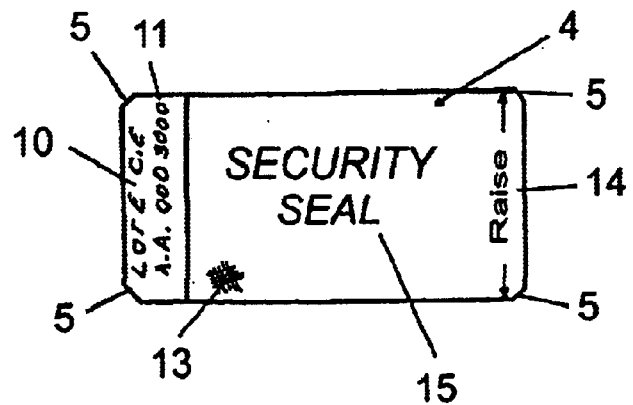
FIG. 9 shows a top perspective view of the device of FIG. 8 with the cover layer entirely closed over the intermediate layer, thus covering and protecting or sheltering the fingerprint in the intermediate layer.

As it is shown in the Figures, cover layer 4 has a hinged edge that is adhered to the intermediate layer by means of an adhesive hinge tape 10 having a lower surface with adhesive and a half portion thereof is adhered to cover layer 4 and the remaining half portion is adhered to the intermediate layer. Thus, cover layer 4 remains attached to layer 3 even when layer 4 is pulled up and peeled off layer 3, as shown in FIGS. 6–8. Tape 10 may include indicia or data corresponding to batch number, etc. which data may be entered into a data processor.

Figure 3:
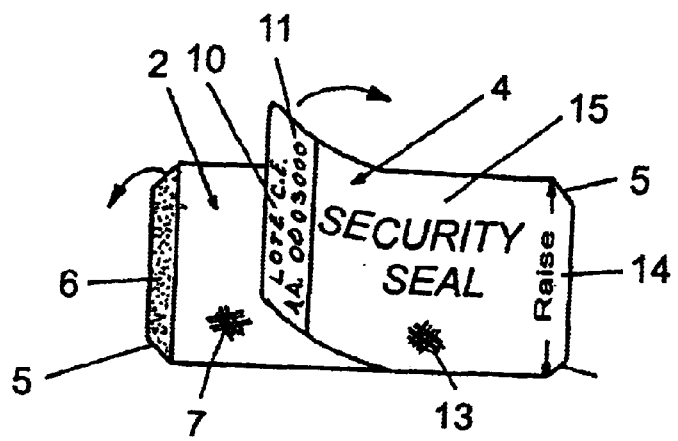
FIG. 3 shows a top perspective view of the device of FIG. 1 with the base layer being partially peeled out from the intermediate layer.

According to one preferred mode of using the device of the invention, tongue 6 is pulling down, as shown in FIG. 3, to peel off base layer 2 and entirely remove layer 2 from the intermediate layer, thus uncovering the lower face of layer 3 containing the adhesive for adhering this face onto the surface of any desired form, document, sheet of paper, ID card, etc., close to the signature of an individual under identification, for example. With a light pressure over layer 4, the adhesive in the lower face of intermediate layer is firmly adhered to the desired substrate.

Figure 4:
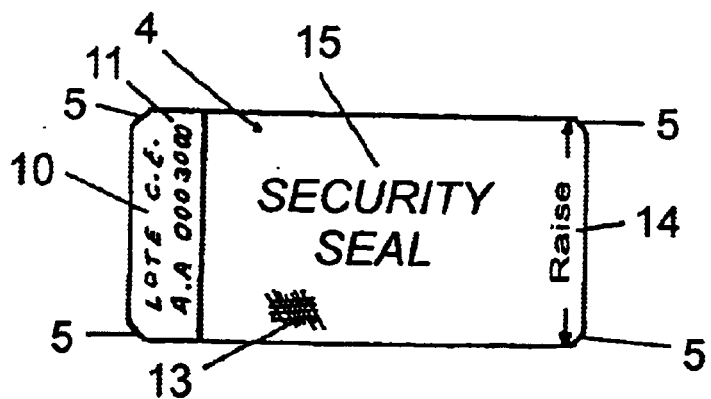
FIG. 4 shows a top plan view of the device of FIG. 1 with the base layer removed and the intermediate layer adhered onto a surface of a document, for example.
Figure 5:
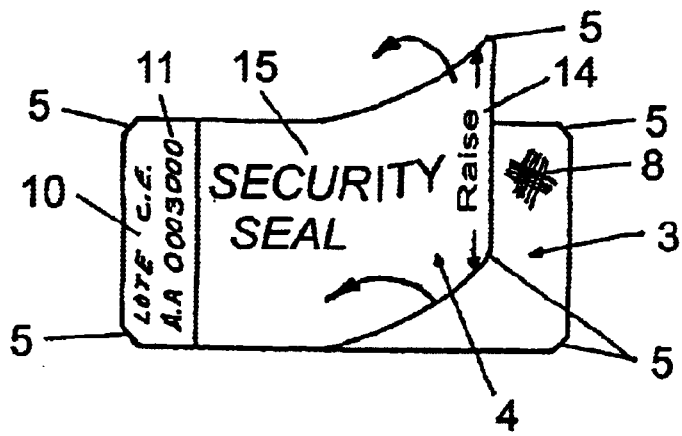
FIG. 5 shows a top perspective view of the device of FIG. 1 with the cover layer being partially peeled up from the intermediate layer.

Once the device of the invention is fixed to a substrate as shown in FIG. 4, cover layer or sheet 4 is taken preferably from the right hand edge thereof, wherein the indicia 14 reading "LEVANTE" is placed, and the sheet is lifted as shown by the arrow in FIGS. 5 and 6 to uncover upper adhesive surface 8 of intermediate layer or sheet 3. Cover sheet 4 will remain hinged to intermediate sheet 3 by hinge tape 10. In this conditions, a finger is placed onto surface 8, as shown in FIG. 7, with a pressure enough to live a print of the finger pulp in the adhesive of layer 3. In addition to the fingerprint several matter and material from the finger, such as particles, dead epidermis cells, sweat, humidity, etc. The fingerprint of the invention, differing from a typical fingerprint obtained through the use of inks, will be provided with additional information such as the depth of the finger pulp grooves, or in other words, the height of the epidermis crests or epithelial lines also useful for measuring the distances between these lines. In addition, the matter and material that was present in the finger and is now retained in the adhesive face of the intermediate layer will provide enough information for determining the individual's DNA.

Layer 4 made of super-calendered glassine Kraft paper not only prevents the adhesive from being spoiled up to the moment when the fingerprint is obtained but also will preserve the fingerprint once the cover sheet is closed down, as it is shown by the arrow in FIG. 8, over surface 8 of layer 3. This protection and shelter of the fingerprint is enhanced by the fact that lower face 9 is treated with paraffin to be capable of being peeled off again as desired, thus preventing the sheet from getting firmly adhered to intermediate layer 3.

Corners 5 are cut or slant as shown in order to prevent the corners from being undesirable plied. The properties and features of outer face 13 of cover sheet 4 permits the addition of indicia, marks, logos etc. This indicia may include indications for operating the device such as "LIFT" or "LEVANTE" as indicated by reference 14, or batch numbers as indicated by reference 11 which number may be entered into a data base of a processor, software of "Pin-Out" for the web, or in any other place as desired.

It will be obvious for any person skilled in the art that the device of the invention may be obtained or manufactured through any industrial process such as a process of printing, process of labeling, process of making documents, process for making multi-key carton cards (PIN-OUT). In addition, the finger print recorded in the intermediate layer can be scanned by an OCR, or may be picked up by any conventional method by using fine powder and brushes.

While preferred embodiments of the present invention have been illustrated and described, it will be obvious to those skilled in the art that various changes and modifications may be made therein without departing from the scope of the invention as defined in the appended claims.

I claim:

1. A safety identification device for collecting and preserving fingerprints and DNA related material from an individual, for use in verifying the identity of the individual, the device comprising:

a base layer comprising a base sheet made of high resistant high density glassine super-calendered kraft paper having an inner silicone treated smooth semi-glossy face, an intermediate layer for collecting and retaining a fingerprint, particles and debris from a finger of the individual, the particles and debris being apt to determine the DNA of the individual, and a cover layer for covering and sheltering the fingerprint, particles and debris retained in the intermediate layer, the base layer, the intermediate layer and the cover layer being attached into one peelable arrangement and the base sheet having a trapezoidal tongue extending from an end of the base sheet and in the same plane of the base sheet for peeling out the base sheet from the peelable arrangement.

2. The device of claim 1, wherein the device is rectangular with corners slant at 135°, with long sides having 55–65 mm and short sides having 25–35 mm.

3. The device of claim 2, wherein the tongue extends about 3 mm out from the base layer and the kraft paper has a weight of 76–85 g/square meter, a longitudinal tensile strength of 1.5–20 Kg/inch, and a transverse tensile strength of 7.5–11 Kg/inch.

4. The device of claim 1, wherein the intermediate layer is a double face support material comprising a non thermally sealable polypropylene film having two treated faces, the film having a tensile strength of 1400 kg/square inch, a weight of about 11 kg/square meter, a thickness of about 12.5$\mu$ and a crystal color.

5. The device of claim 4, wherein the two faces of the intermediate layer film defines an upper face and a lower face, both faces provided with an adhesive, the adhesive comprising an aqueous dispersed acrylate polymer modified with synthetic components and having an adhesiveness of 750 g/inch, the adhesive being semi-hard to hard, and having high cohesive properties at 24 h. and a loop tack of 950 g/inch, the lower face being applicable to any surface to be adhered thereto, the adhesive in the upper face permitting to put a finger tip to obtain a fingerprint with clear epithelial lines, the fingerprint retaining detailed thickness and depth of said lines as well as retaining epithelial particles and debris, dead cells, finger skin humidity, finger skin fat, all for determining the DNA of an individual finger.

6. The device of claim 5, wherein the base layer is adhered to the lower face of the intermediate layer film and the cover layer is adhered to the upper face of the intermediate layer film.

7. The device of claim 6, wherein the cover layer is a high strength, high density glassine-type super-calendered kraft paper having a generally crystalline-white color, with a weight of 62–67 g/square meter, a thickness of 55.8 $\mu$ and a breaking strength of 17 kg/inch, the paper having an outer face and an inner face, the outer face being transparent and provided with silicone for receiving a printed indicia, and the inner face being treated with paraffin to prevent the paper from being adhered to the adhesive-containing upper face of the intermediate layer film.

8. The device of claim 7, wherein the indicia comprises code numbers and personal data for storing in a data base and a computer.

9. The device of claim 5, wherein the base layer and the cover layer protects the lower and upper faces of the intermediate layer, respectively, thus preventing these faces from being adhered to the layers and preserving the adhesive properties of the adhesive up to the moment the device is used.

10. The device of claim 1, wherein the cover layer has a hinged edge that is adhered to the intermediate layer by means of an adhesive hinge tape having a half portion thereof adhered to the cover layer and a remaining half portion adhered to the intermediate layer.

11. A safety identification device for collecting and preserving fingerprints and DNA related material from an individual, for use in verifying the identity of the individual, the device comprising:

a base layer, an intermediate layer for collecting and retaining a fingerprint, particles and debris from a finger of the individual, the particles and debris being apt to determine the DNA of the individual, and a cover layer for covering and sheltering the fingerprint, particles and debris retained in the intermediate layer, the intermediate layer being a double face support material comprising a non thermally sealable polypropylene film having two treated faces, the film having a tensile strength of 1400 kg/square inch, a weight of about 11 kg/square meter, a thickness of about 12.5 $\mu$ and a crystal color.

12. The device of claim 11, wherein the two faces of the intermediate layer film defines an upper face and a lower face, both faces provided with an adhesive, the adhesive comprising an aqueous dispersed acrylate polymer modified with synthetic components and having an adhesiveness of 750 g/inch, the adhesive being semi-hard to hard, and having high cohesive properties at 24 h. and a loop tack of 950 g/inch, the lower face being applicable to any surface to be adhered thereto, the adhesive in the upper face permitting to put a finger tip to obtain a fingerprint with clear epithelial lines, the fingerprint retaining detailed thickness and depth of said lines as well as retaining epithelial particles and debris, dead cells, finger skin humidity, finger skin fat, all for determining the DNA of an individual finger.

13. The device of claim 12, wherein the base layer is adhered to the lower face of the intermediate layer film and the cover layer is adhered to the upper face of the intermediate layer film.

14. The device of claim 13, wherein the cover layer is a high strength, high density glassine-type super-calendered kraft paper having a generally crystalline-white color, with a weight of 62–67 g/square meter, a thickness of 55.8$\mu$ and a breaking strength of 17 kg/inch, the paper having an outer face and an inner face, the outer face being transparent and provided with silicone for receiving a printed indicia, and the inner face being treated with paraffin to prevent the paper from being adhered to the adhesive-containing upper face of the intermediate layer film.

15. The device of claim 14, wherein the indicia comprises code numbers and personal data for storing in a data base and a computer.

16. The device of claim 12, wherein the base layer and the cover layer protects the lower and upper faces of the intermediate layer, respectively, thus preventing these faces from being adhered to the layers and preserving the adhesive properties of the adhesive up to the moment the device is used.

* * * * *